(12) United States Patent
Pancholy et al.

(10) Patent No.: US 9,408,611 B1
(45) Date of Patent: *Aug. 9, 2016

(54) APPARATUS AND METHOD TO STOP BLEEDING

(71) Applicants: Samir Bipin Pancholy, Clarks Summit, PA (US); Nolan Rajendra Sardesai, Arcadia, CA (US); Milind Padmakar Panse, Riverside, CA (US); Rajendra Gurudas Sardesai, Arcadia, CA (US)

(72) Inventors: Samir Bipin Pancholy, Clarks Summit, PA (US); Nolan Rajendra Sardesai, Arcadia, CA (US); Milind Padmakar Panse, Riverside, CA (US); Rajendra Gurudas Sardesai, Arcadia, CA (US)

(73) Assignee: VASOINNOVATIONS, INC., South Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/093,739

(22) Filed: Apr. 8, 2016

Related U.S. Application Data

(63) Continuation of application No. 14/819,383, filed on Aug. 5, 2015, now Pat. No. 9,332,994.

(51) Int. Cl.
*A61B 17/00* (2006.01)
*A61B 17/132* (2006.01)
*A61B 17/135* (2006.01)

(52) U.S. Cl.
CPC .......... *A61B 17/1325* (2013.01); *A61B 17/135* (2013.01)

(58) Field of Classification Search
CPC ............. A61B 17/1325; A61B 17/135; A61B 17/132; A61B 17/1322; A61B 2017/00902; A61B 2017/120034; A61F 2013/00829

USPC ............... 606/201–203; 601/132, 151, 33, 40
See application file for complete search history.

(56) References Cited

U.S. PATENT DOCUMENTS

| | | | |
|---|---|---|---|
| 37,156 | A | 12/1862 | Dunton |
| 3,905,361 | A | 9/1975 | Hewson et al. |
| 4,863,429 | A | 9/1989 | Baldwin |
| 4,920,971 | A | 5/1990 | Blessinger |

(Continued)

FOREIGN PATENT DOCUMENTS

| EP | 0 601 756 A1 | 6/1994 |
|---|---|---|
| WO | WO 97/02783 A1 | 1/1997 |

OTHER PUBLICATIONS

Samir Pancholy, et al, "Prevention of Radial Artery Occlusion—Patent Hemostasis Evaluation Trial (Prophet study)" Catheterization and Cardiovascular Interv 72:335-340 (2008).

(Continued)

*Primary Examiner* — Sarah W Aleman
*Assistant Examiner* — Socrates L Boutsikaris
(74) *Attorney, Agent, or Firm* — Rajendra Sardesai

(57) ABSTRACT

A hemostatic device is provided to stop bleeding at a puncture site on the wrist of a patient, the device comprising a transparent flexible band to be wrapped at the site where the bleeding is to be stopped, a curved frame having an inner peripheral side and possessing a first curved portion in its first half and a second curved portion in its second half, a first balloon provided on the inner peripheral side in the first half of the curved frame and a second balloon provided on the inner peripheral side in the second half of the curved frame, the first balloon being larger than the second balloon. The bleeding from radial artery is stopped by compressing the radial artery at the puncture site using inflation of the first balloon and radial artery flow is increased by compression of ipsilateral ulnar artery using inflation of the second balloon.

30 Claims, 9 Drawing Sheets

(56) References Cited

U.S. PATENT DOCUMENTS

| | | | |
|---|---|---|---|
| 4,981,133 | A | 1/1991 | Rollband |
| 5,152,302 | A | 10/1992 | Fareed |
| 5,295,951 | A | 3/1994 | Fareed |
| 5,307,811 | A | 5/1994 | Sigwart et al. |
| 5,464,420 | A | 11/1995 | Hori et al. |
| 5,486,194 | A | 1/1996 | Kawasaki et al. |
| 5,496,262 | A | 3/1996 | Johnson et al. |
| 5,514,155 | A | 5/1996 | Daneshvar |
| 5,569,297 | A | 10/1996 | Makower et al. |
| 5,643,315 | A | 7/1997 | Daneshvar |
| 5,660,182 | A | 8/1997 | Kuroshaki et al. |
| 5,792,173 | A | 8/1998 | Breen et al. |
| 5,840,037 | A | 11/1998 | Tochikubo et al. |
| 6,007,562 | A | 12/1999 | Harren et al. |
| 6,336,901 | B1 | 1/2002 | Itonaga et al. |
| 6,361,496 | B1 | 3/2002 | Zikorus et al. |
| 6,527,727 | B2 | 3/2003 | Itonaga et al. |
| 6,694,821 | B2 | 2/2004 | Yamakoshi et al. |
| 6,827,727 | B2 | 12/2004 | Stalemark et al. |
| 7,498,477 | B2 | 3/2009 | Wada et al. |
| 7,927,295 | B2 | 4/2011 | Bates et al. |
| 8,034,009 | B2 | 10/2011 | Bates et al. |
| 8,152,776 | B2 | 4/2012 | McCluskey |
| 8,481,803 | B2 | 7/2013 | Wada et al. |
| 8,481,805 | B2 | 7/2013 | Wada et al. |
| 2002/0147404 | A1 | 10/2002 | Kato |
| 2003/0199922 | A1 | 10/2003 | Buckman |
| 2004/0049214 | A1 | 3/2004 | Akerfeldt |
| 2004/0098035 | A1 | 5/2004 | Wada et al. |
| 2004/0122469 | A1 | 6/2004 | Akerfeldt |
| 2005/0153090 | A1 | 7/2005 | Marchitto |
| 2009/0138039 | A1 | 5/2009 | Wada et al. |
| 2009/0281565 | A1 | 11/2009 | McNeese |
| 2012/0296369 | A1 | 11/2012 | Atthoff et al. |
| 2013/0116725 | A1 | 5/2013 | Wada et al. |
| 2013/0178894 | A1 | 7/2013 | Wada et al. |
| 2013/0304111 | A1* | 11/2013 | Zhadkevich ....... A61B 17/1325 606/202 |
| 2014/0142615 | A1 | 5/2014 | Corrigan, Jr. |
| 2015/0018869 | A1 | 1/2015 | Benz |

OTHER PUBLICATIONS

Samir B. Pancholy, "Transradial Access in an Occluded Radial Artery: New Technique" Journal Invasive Cardiology, vol. 19, Issue 12, Dec. 2007.

Samir B. Pancholy, "Transradial Approach" Angioplasty.Org Interview Series, 3 pages, Aug. 2008.

Samir B. Pancholy, "Impact of Two Different Hemostatic Devices on Radial Artery Outcomes after Transradial Catheterization" J Invasive Cardiology,vol. 21,Issue 3, Mar. 2009.

Ivo Bernat, et al, "Efficacy and Safety of Transient Ulnar Artery Compression to Recanalize Actute Radial Artery Occlusion . . . " Am J Cardiol,107:1698-1701(2011).

Samir B. Pancholy, "Strategies to Prevent Radial Artery Occlusion After Transradial PCI" Curr Cardiol Rep, 16:505, Jun. 2014.

Patel, T. et al, "Balloon-assisted tracking: A must-know technique . . . " Cath. Cardio. Interv., Wileyonlinelibrary.com; DOI:10.1002/ccd.24959, Apr. 2013.

Kwan, T. et al, "Transulnar catheterization in patients with ipsilateral radial artery occlusion" Cath Cardio Interv, Wileyonlinelibrary.com, DOI 10.1002/ccd.24662 Sep. 2012.

Patel, T. et al, "Balloon-assisted tracking of a guide catheter . . . : A technical report" Cath. Cardio. Interv., Wileyonlinelibrary.com; DOI 10.1002/ccd.24504, May 2012.

Kwan, T. et al. "Feasibility and safety of 7F sheathless guiding catheter during transradial coronary intervention", Wileyonlinelibrary.com; DOI 10.1002/ccd.24310, Aug. 2012.

Pancholy, S et al, "Comparison of a priori versus provisional heparin therapy on radial artery occlusion . . . (Pharaoh Study)", Am J Cardiol, vol. 110(2), p. 173-176 Jul. 2012.

Pancholy, S et al, "Radial artery access technique evaluation trial: randomized comparison . . .", Catheter Cardiovasc Interv., vol. 80(2), p. 288-91, Aug. 2012.

Pancholy, S et al, "Effect of duration of hemostatic compression on radial artery occlusion after transradial access", Catheter Cardio Interv, vol. 79(1), p. 78-81, Jan. 2012.

Caputo, R, et al, "Transradial arterial access for coronary and peripheral procedures . . . " Catheter Cardiovasc Interv., vol. 78(6), p. 823-39, Nov. 2011.

Bertrand, O et al, "Transradial approach for coronary angiography and interventions . . . ", JACC Cardiovasc Interv., vol. 3(10), p. 1022-31 Oct. 2010.

Pancholy, S et al, "Comparison of door-to-balloon times for primary PCI using transradial versus transfemoral approach" Catheter Cardio Interv. vol. 75(7), p. 991-5 Jun. 2010.

Patel, T. et al, "Contralateral transradial approach for carotid artery stenting: a feasibility study" J. Catheter Cardiovasc Interv. vol. 75(2), p. 268-75. Feb. 2010.

Pancholy, S. "Comparison of the effect of intra-arterial versus intravenous heparin on radial artery occlusion . . . " Am J Cardiol. vol. 104(8) p. 1083-5 Oct. 2009.

Pancholy, S. "Prevention of Radial Artery Occlusion:Prophylactic Hyperperfusion Evaluation Trial ( Prophet-II)" ClinicalTrial.Gov, Protocol Registration System, Mar. 2012.

Pancholy, S. et al, "Subcutaneous administration of nitroglycerin to facilitate radial artery cannulation" Catheter Cardiovasc Interv. vol. 68(3) p. 389-9, Sep. 2006.

Mamas, M, "Dissection, Occlusion, and Spasm; Myths Involving Sheathless Guide Catheters" Catheterization and Cardiovascular Interventions 76:777-778, Feb. 2010.

Pancholy, S "Hemostasis and Radial Artery Patency", Presentation, http://www.slideshare.net/theradialist/pancholy-sb-201111, Jan. 2012.

Shroff, A et al "Comparing radial with femoral artery access in patients with ST-segment elevation myocardial infarction . . . " Expert Rev Cardio Ther. 11(5):525-7, May 2013.

Patel, T et al "Coronary cannulation through mirror-image right aortic arch during right transradial approach . . . " J Invasive Cardiol. 24(5):234-5, May 2012.

Kwan, T. et al "Balloon-assisted sheathless transradial intervention (BASTI) using 5 Fr guiding catheters" J Invasive Cardiol. 24(5):231-3, May 2012.

Dharma, S. et al "Nitroglycerin plus diltiazem versus nitroglycerin alone for spasm prophylaxis with transradial approach" J Invasive Cardiol. 24(3):122-5, Mar. 2012.

Pancholy, S et al "A technique to access difficult to find upper extremity veins for right heart catheterization . . . " Catheter Cardiovasc Interv., 78(5):809-12, Nov. 2011.

Patel, T et al, "Reaccessing an occluded radial artery: a "proximal entry" technique" J Interv Cardiol. 24(4):378-81, Aug. 2011.

Patel, T et al, "Management of radial and brachial artery perforations during transradial procedures . . . " J Invasive Cardiol. 21(10):544-7, Oct. 2009.

Patel, T et al, "A simple approach for the reduction of knotted coronary catheter in radial artery during transradial approach" J Invasive Cardiol. 23(5):E126-7, May 2011.

Examiner's Search in priority U.S. Appl. No. 13/941,219, filed Jul. 12, 2013—Other References Patent.

Examiner's Search in priority U.S. Appl. No. 13/941,219, filed Jul. 12, 2013—Other References NPL.

Examiner's Search in priority U.S. Appl. No. 13/941,219, filed Jul. 12, 2013—Other References Inventor.

* cited by examiner

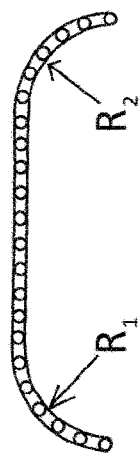
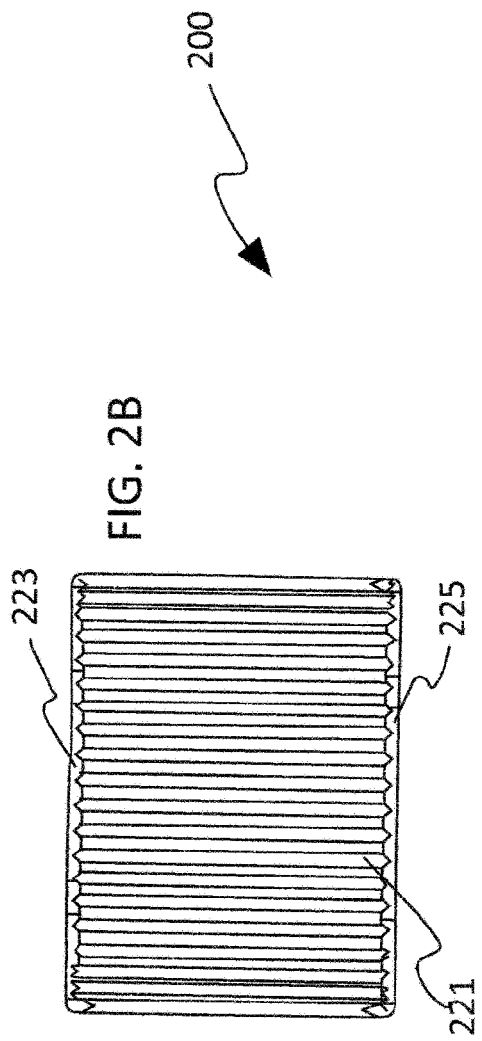
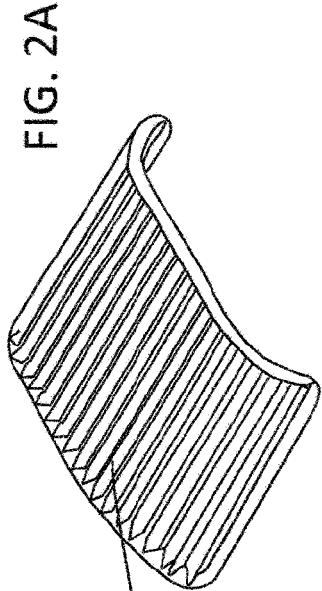

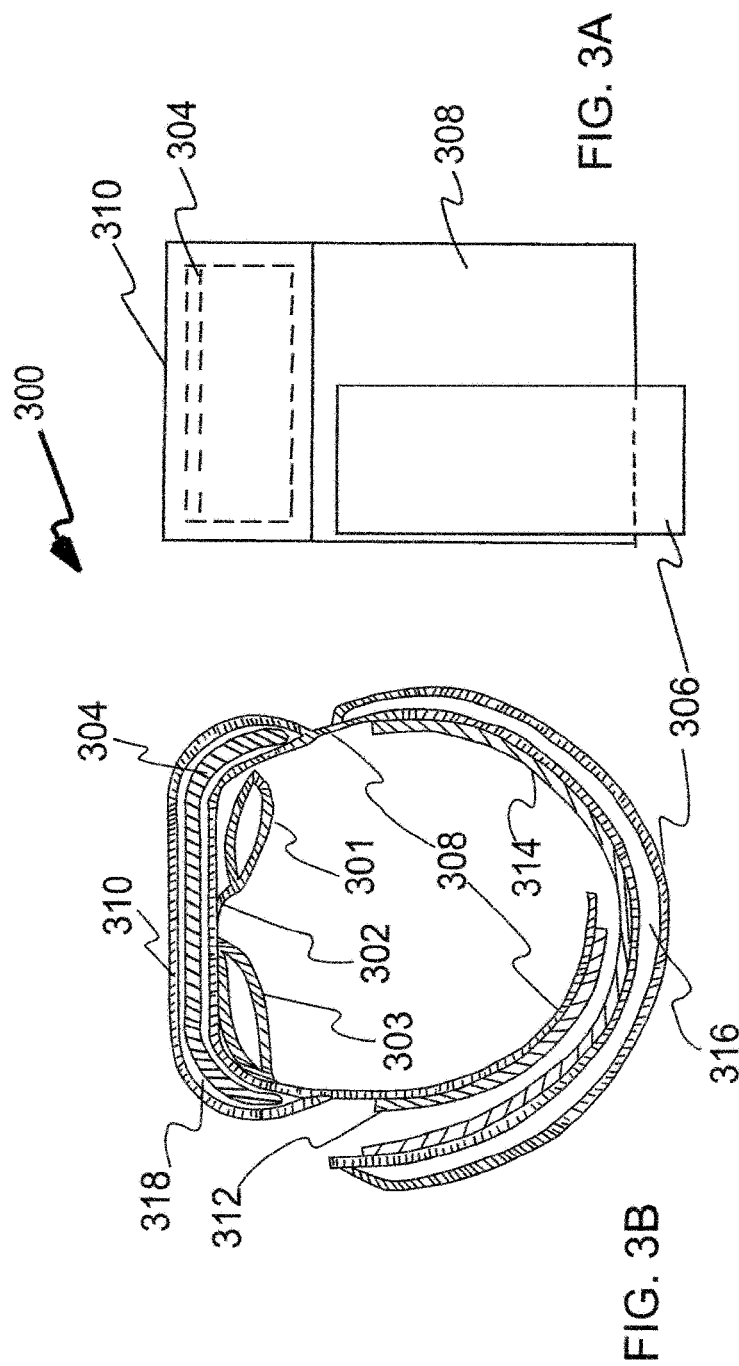

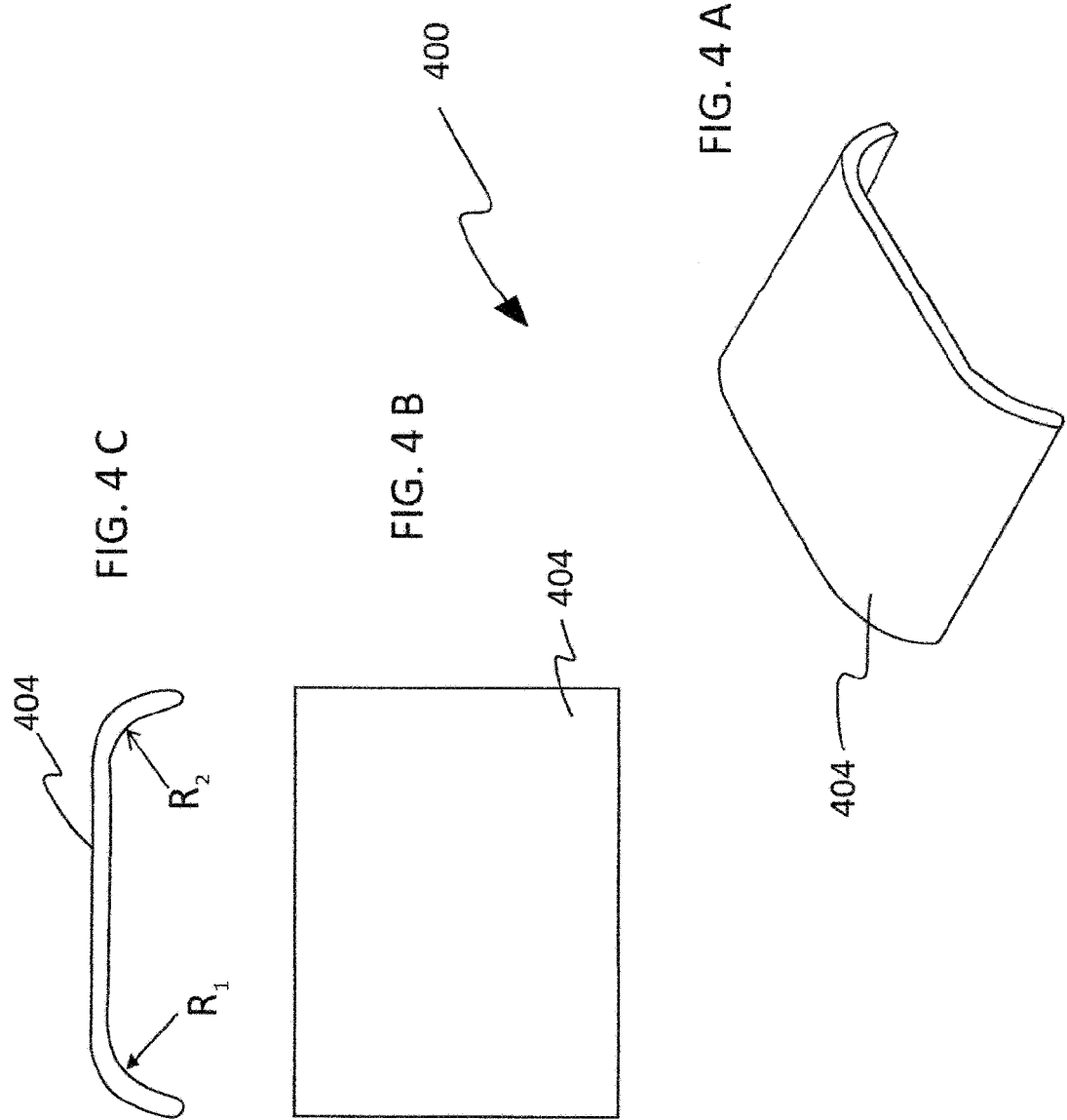

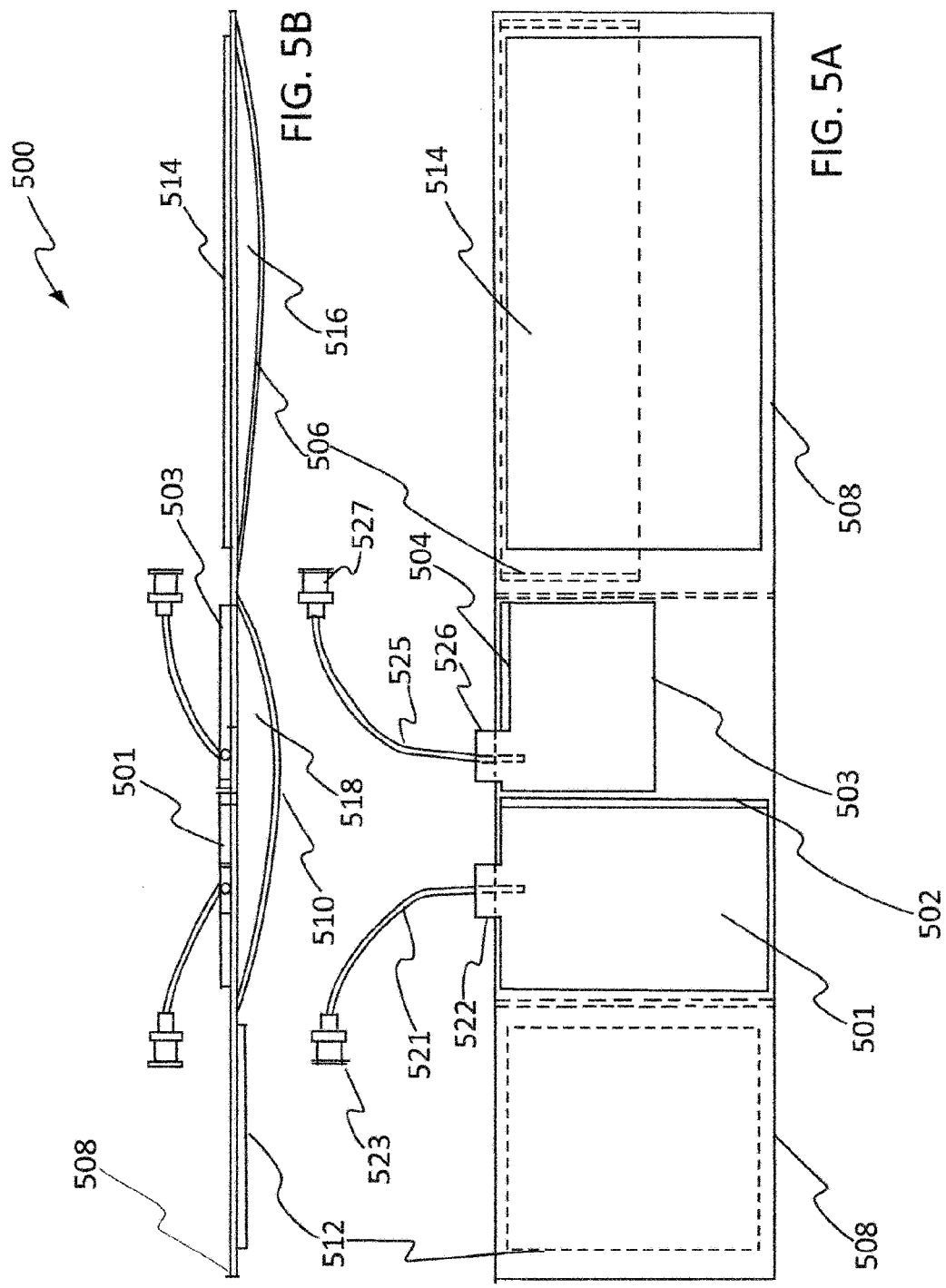

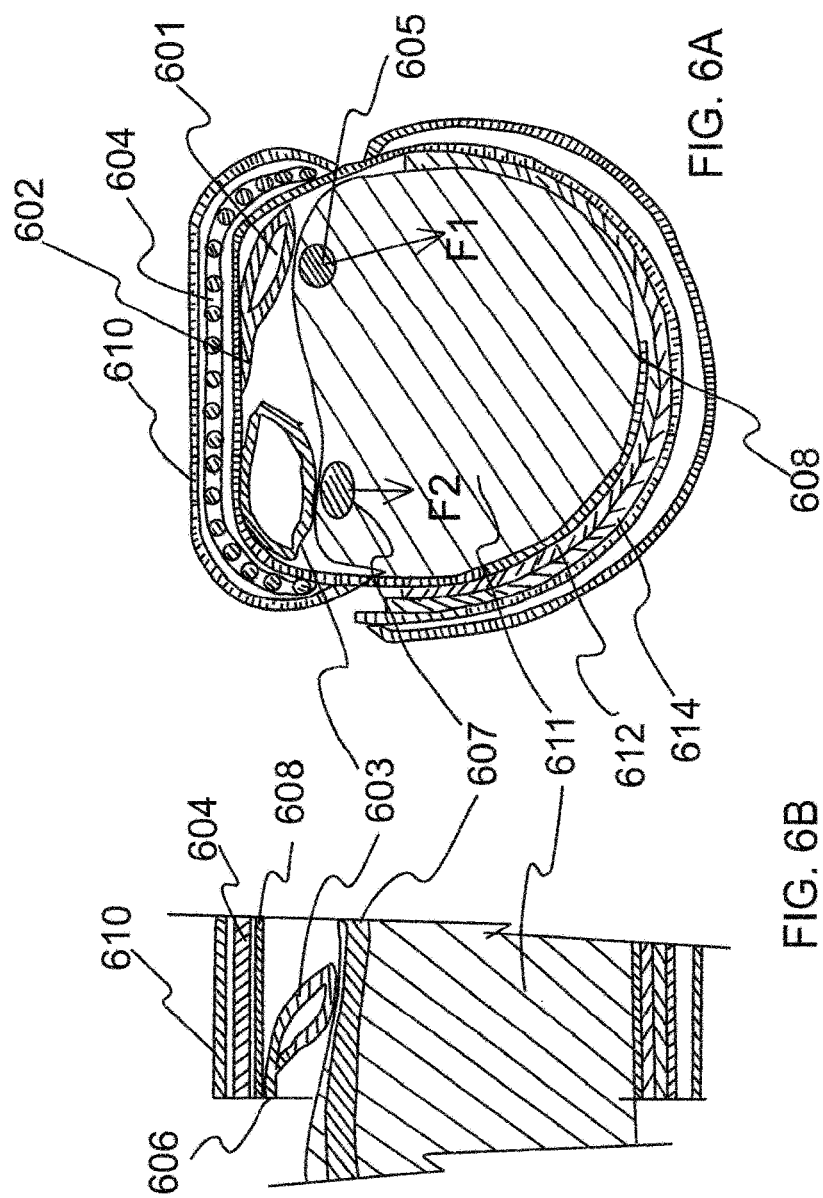

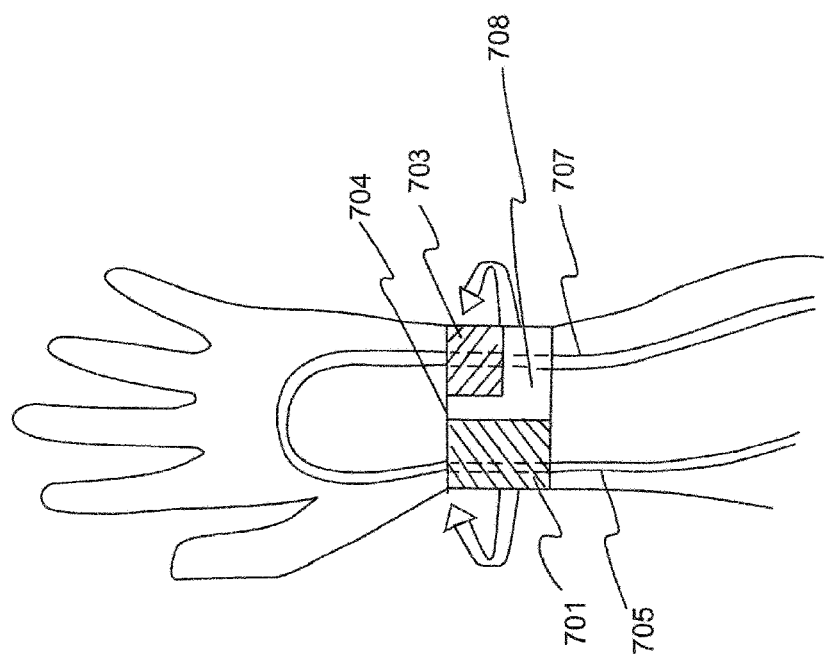

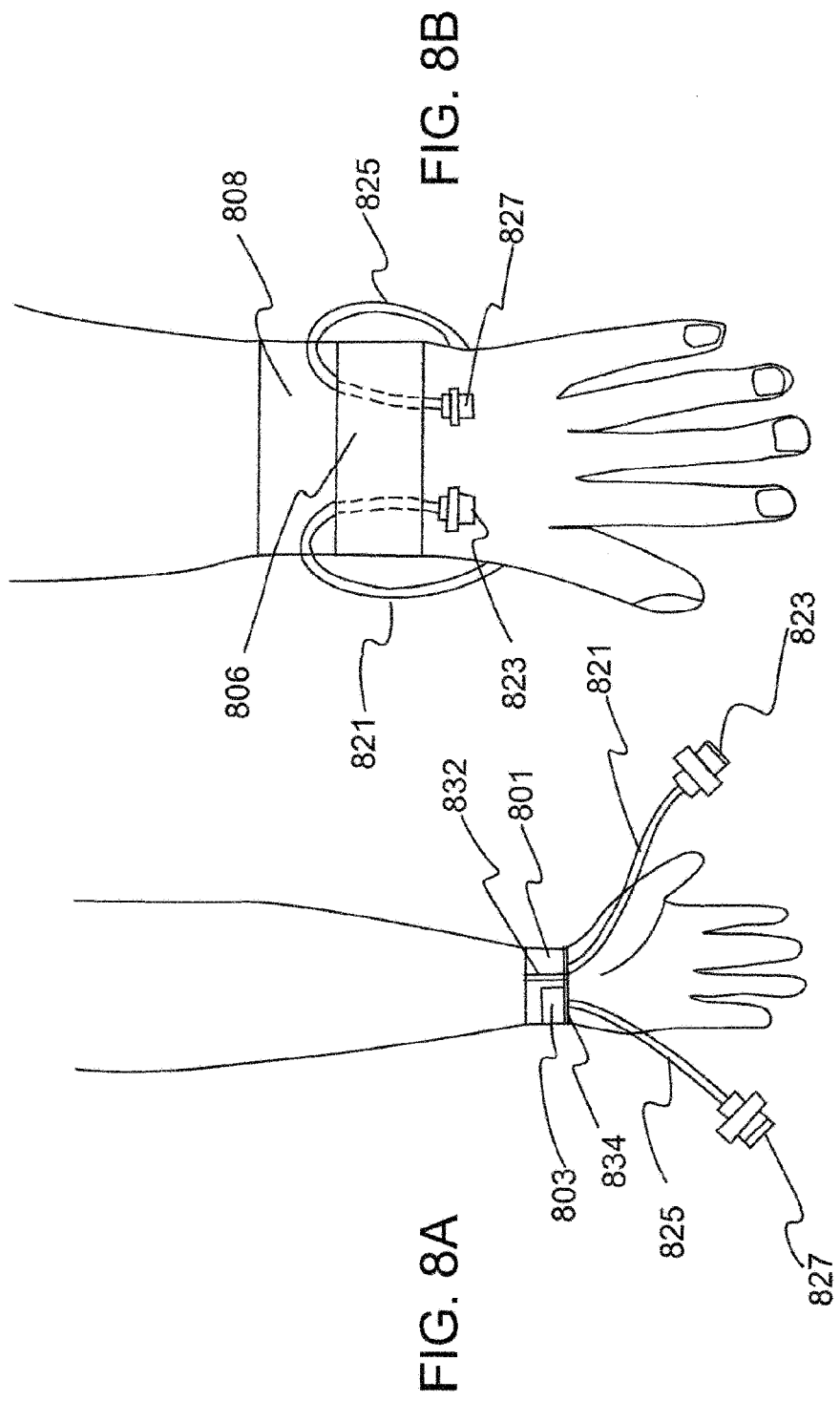

APPARATUS AND METHOD TO STOP BLEEDING

CROSS-REFERENCE TO RELATED APPLICATIONS

This application is a continuation of co-pending application
U.S. patent application Ser. No. 14/819,383, filed Aug. 5, 2015, which claims the benefit of the earlier filing dates of the following applications
U.S. patent application Ser. No. 13/941,219, filed Jul. 12, 2013;
U.S. Provisional Patent Application No. 62/089,281, filed Dec. 9, 2014;
U.S. Provisional Patent Application No. 62/096,857, filed Dec. 25, 2014;
U.S. Provisional Patent Application No. 62/103,063, filed Jan. 13, 2015;
U.S. Provisional Patent Application No. 62/142,195, filed Apr. 2, 2015;
U.S. Provisional Patent Application No. 62/157,419, filed May 5, 2015.

FIELD

Embodiments described herein concern devices and methods for obtaining hemostasis after puncturing a blood pathway, including without limitation puncture of radial or ulnar artery.

BACKGROUND

Blood vessel puncture is commonly needed for performance of endovascular procedures. Smaller caliber arteries, including radial, ulnar and pedal arteries, are easier to manage after the procedure because bleeding can be controlled more easily with external pressure. However, occlusion of these arteries occurs more frequently compared to larger arteries, which frequently results in permanent loss of patency.

Radial artery occlusion refers to the blockage of the radial artery and is a consequence of radial artery cannulation that obliterates the radial artery lumen. Hemostatic devices, which are attached by being wrapped around the portion of an arm where the puncture site (also referred to as the access site) is located and compress the puncture site where bleeding is to be stopped, are already known in the prior art (e.g., U.S. Pat. No. 7,498,477 B2, U.S. Pat. No. 8,481,803, U.S. Pat. No. 8,481,805, JP 3,031,486 U). In prior-art hemostatic devices, pressure applied to the puncture site may lead to radial artery occlusion making it not available for access in the future.

Radial artery occlusion, after transradial access occurs in 2-10% of patients, and is frequently associated with obliteration of radial artery lumen, making that radial artery not suitable for future access for endovascular procedures, invasive monitoring, or its utility as a bypass conduit. Prevention of radial artery occlusion is of paramount importance to avoid loss of a major source of blood supply, future repeat access and other utilities of radial artery, after transradial access. Maintenance of radial artery flow during hemostatic compression has been shown to lower the risk of radial artery occlusion (PROPHET Trial, Pancholy S et al, Catheterization and Cardiovascular Interventions 2008:72(3); 335-340). A decrease in duration of compression has also been shown to lower the risk of radial artery occlusion (Pancholy S et al, Catheterization and Cardiovascular Interventions 2012:79(1):78-81). Thus maintaining blood flow in the radial artery, while compressing the access site after instrumentation, is known to reduce the risk of post-instrumentation radial artery occlusion. Patent hemostasis is therefore understood to mean achieving the cessation of bleeding at the cannulation wound (access site) of the radial artery, while blood is allowed to flow through that artery.

In an article entitled Efficacy and Safety of Transient Ulnar Artery Compression to Recanalize Acute Radial Artery Occlusion After Transradial Catheterization (Am J Cardiol 2011; 107:1698-1701) Ivo Bernat, M D and others discuss a method directed to open an occluded radial artery after the radial artery becomes occluded. In this study, in patients with radial artery occlusion, 3-4 hours after hemostasis of the radial artery, ulnar artery compression was applied to attempt recanalization of radial artery. Bernat et. al. achieved higher success rates at reopening of the radial artery by administration of heparin and compression of the ipsilateral ulnar artery.

SUMMARY

Transradial, as well as transulnar, puncture is increasingly used for obtaining vascular access for endovascular procedures. In one embodiment, a hemostatic device comprises two balloons wherein, after transradial access, the bleeding from the radial artery is stopped by compressing the radial artery at the puncture site using inflation of a first balloon and the radial artery flow is increased by occlusive compression of ipsilateral ulnar artery using inflation of a second balloon. The method maintains blood flow in the radial artery while compressing the access site, after removal of catheter, thereby reducing the risk of post-instrumentation radial artery occlusion. In one embodiment, the first balloon is located over the radial artery to cover a puncture site that is generally about 2 cm. from the base of a palm, and the second balloon is located over the ulnar artery at a position proximate to the base of the palm (Guyon's canal) thereby compressing the ulnar artery at a location where it is most accessible for compression.

In another embodiment, two balloons are part of a band and the band is wrapped around a limb. The center of the first balloon and the center of the second balloon are offset from each other in relation to the central line of axis of the band. In yet another embodiment, the first balloon is larger than the second balloon. In another embodiment, the balloons are rectangular in shape. In one embodiment the first balloon extends the entire width of the band. In one embodiment, the width of the band is greater than 40 mm. In another embodiment, the width of the band is greater than 45 mm. In yet another embodiment, the band has a width of about 55 mm.

In another embodiment, the hemostatic device comprises a flexible band adapted to be wrapped and secured around a hand of a patient at a site on the hand where bleeding is to be stopped, a compression member having an inner peripheral side, which compression member is made of a material more rigid than the band, a first balloon provided on the inner peripheral side at a position deviated to the center portion of the compression member in lengthwise direction of the band, and the first balloon is connected to the band by a connector on a side of the first balloon adjacent the center portion of the compression member, wherein the first balloon inflates when a fluid is introduced therein; and a second balloon provided on the inner peripheral side of the compression member at a position deviated to an edge of the compression member from the center portion of the compression member in widthwise direction of the band, and the second balloon is connected to the band by a connector on a side of the second balloon adjacent to the edge of the compression member, wherein the second balloon inflates when a fluid is introduced therein. In one embodiment, the compression member is a curved frame with rungs. In some embodiments, rungs may be equidistant from each other along the length of the frame. In other embodiments, the rungs may be staggered whereby some rungs are close to each other while the others are spread out. In yet another embodiment, the compression member is a curved plate.

In some embodiments, at least a portion of the compression member is curved toward the inner peripheral side at proximal and distal ends of the compression member. In one embodiment, the radius of curvature of the compression member at proximal end is nearly the same as radius of curvature of the compression member at distal end. In another embodiment, the compression member may have a contoured shape whereby the band presses snugly the wrist and the base of the palm, and the contoured shape facilitates compression of the ulnar artery at the base of the palm.

In operation, a method of catheterization of the radial artery comprises inserting a sheath into the radial artery of a patient at an access site. The desired catheterization procedure is then performed using the sheath or catheter to access the radial artery. Once the catheterization procedure is complete, an ulnar pressure is applied to the ipsilateral ulnar artery at an ulnar pressure site while the sheath remains inserted in the radial artery. The sheath is then removed from the radial artery while maintaining the ulnar pressure to the ulnar artery. Once the sheath is removed, and while continuing to apply the ulnar pressure, pressure is applied to the radial artery at the access site to obtain hemostasis at the access site. In another embodiment, application of pressure to the radial artery at the access site to obtain hemostasis at the access site is accomplished while maintaining the ulnar pressure to the ulnar artery.

In another embodiment, vasodilator medication such as nitroglycerine is disposed on at least a portion of the skin-contacting surface of the balloon pressing on the puncture site to reduce spasm. Spasm may play a role in the process of interruption of the flow, which then leads to thrombosis and resultant lumen obliteration with fibrosis. Prevention and relief of spasm may help lower the probability of occlusion.

In yet another embodiment, a composition is disposed on at least a portion of the skin-contacting region of the balloon. The composition includes at least a hydrocolloid component and an oil component. In one embodiment, a release-coated liner is included on the skin-contacting side of the balloon. The liner is retained in place prior to use and is removed just prior to application to user's skin. The release-coated liner may be any release-coated liner known in the art that is compatible with the composition disposed on the skin-contacting side of the balloon.

BRIEF DESCRIPTION OF DRAWINGS

FIG. 2 is a schematic three-dimensional view (FIG. 2A), a schematic top view (FIG. 2B) and a schematic front view (FIG. 2C) of an embodiment of the compression member 200 that is a curved frame with rungs, and comprising rungs 221 located between two curved beams 223 and 225.

FIG. 3 is a schematic front view (FIG. 3A) and a schematic side view (FIG. 3B) of an embodiment of the hemostatic device 300 comprising at least two balloons 301 and 303, and a compression member that is a curved plate 304 and that is placed in a sleeve 318 formed by a covering 310 attached to a strap 308.

FIG. 4 is a schematic three-dimensional view (FIG. 4A), a schematic top view (FIG. 4B) and a schematic front view (FIG. 4C) of an embodiment of the compression member 400 that is a curved plate.

FIG. 5 is a schematic view of hemostatic device 500 with two balloons 501 and 503. FIG. 5A is a schematic top view that shows a side of the device that serves as the inside surface when the device is attached to the wrist of a patient. FIG. 5B is a schematic front view of the device.

FIG. 6 is schematic sectional view showing hemostatic device of FIG. 1 in use. FIG. 6A shows a schematic sectional front view of an embodiment of the hemostatic device applied on a forearm of a patient. The two balloons 601, 603 are located between the forearm of the patient and the strap 608 that goes around the forearm of the patient. FIG. 6B is a schematic sectional side view of a part of the embodiment of the hemostatic device showing balloon 603 pressing on the ulnar artery 607.

FIG. 7 is a schematic view of an embodiment of the hemostatic device showing placement of balloon 701 over radial artery 705 and balloon 703 over ulnar artery 707.

FIG. 8 is a schematic view of an embodiment of the hemostatic device wrapped around the wrist of a patient wherein FIG. 8A is an anterior view and FIG. 8B is a posterior view.

DETAILED DESCRIPTION

Figure 1A:
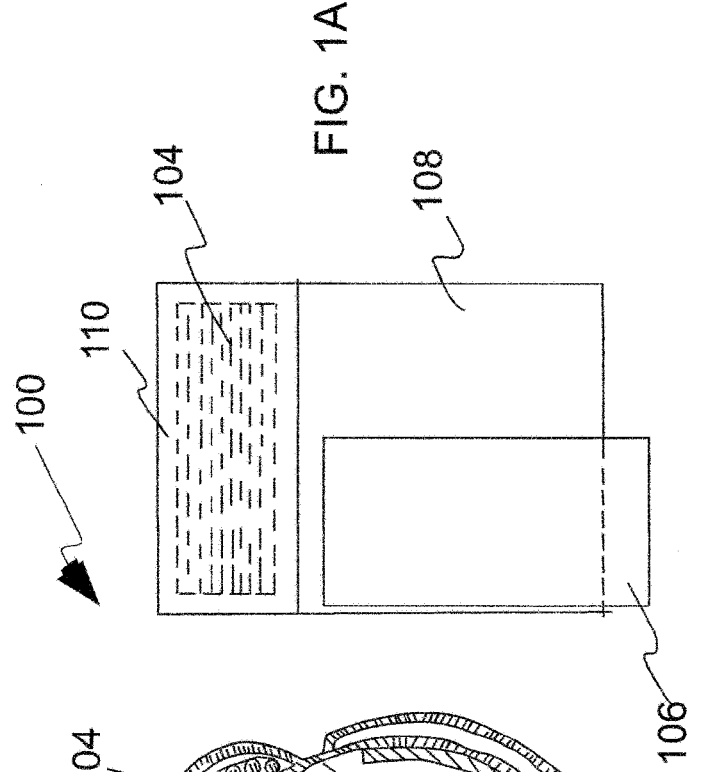
FIG. 1 is a schematic front view (FIG. 1A) and a schematic side view (FIG. 1B) of an embodiment of the hemostatic comprising at least two balloons 101 and 103, and a compression member that is a curved frame with rungs 104 and that is placed in a sleeve 118 formed by a covering 110 attached to a strap 108.

Embodiments described herein provide the user a safe, simple and reliable device and method to apply pressure at the access site of artery, e.g., radial artery to obtain hemostasis and also to apply pressure to another artery, e.g., ulnar artery using the same device.

In one embodiment of the invention (see FIG. 1), hemostatic device 100 is a flexible band comprising a flexible strap 108 adapted to be wrapped and secured by binders 112 and 114 around the wrist of a patient at a puncture site on the hand where bleeding is to be stopped, a curved frame 104, a first balloon 101, and a second balloon 103. The curved frame 104 has an inner peripheral side and is made of a material such that the frame is more rigid than the flexible strap 108. In one embodiment, the frame is made of hard plastic and substantially fixed in shape. In another embodiment, the frame is made of material (e.g. plastic) that is bendable so that the frame does not maintain a substantially fixed shape and flexes with the balloons as the balloons expand and contract with pressure. At least a portion of the frame is curved toward the inner peripheral side. The first balloon 101 is provided on the inner peripheral side at a position deviated to the center portion of the curved frame from the first end of the curved frame in lengthwise direction of the band, and the first balloon is connected to the strap 108 by a connector 102 on a side of the first balloon adjacent the center portion of the curved frame. The first balloon inflates when a fluid is introduced therein. The second balloon 103 is provided on the inner peripheral side of the curved frame at a position deviated to an edge of the curved frame from the center portion of the curved frame in widthwise direction of the band, and the second balloon is connected to the strap 108 by a connector (not shown) on a side of the second balloon adjacent the edge of the curved frame. The second balloon 103 inflates when the fluid is introduced therein. In one embodiment, the band 100 is adapted to be wrapped around the wrist with a surface fastener, e.g., Hook and Loop 112 and 114 for securing the band around the wrist. In some embodiments, pledgets (not shown) are provided for patient comfort. In one embodiment, the pledgets are made of foam.

Figure 1B:
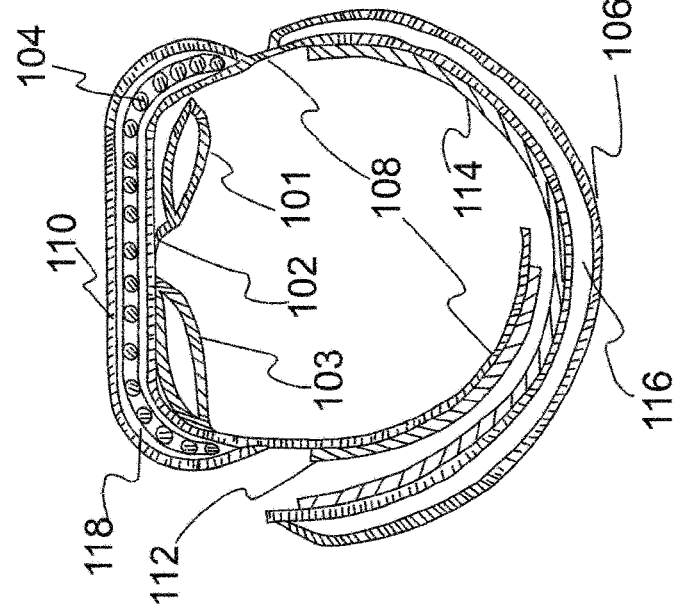

In one embodiment, band may have a first sleeve for holding the frame 104. In the embodiment shown in FIG. 1, the first sleeve is a double layer construction formed by connecting a piece of film 110 to strap 108 of the band at a center portion of the band. The connection may be done by a suitable method such as welding (e.g., heat welding, high-frequency welding, ultrasonic welding) or adhesion/gluing (such as with an adhesive or solvent) so as to form a double layer construction. The frame 104 is inserted into a gap 118 in the double layer and thereby held. In one embodiment, in addition to the center portion of the band, at least one side end portion of the band has a sleeve. As shown in FIG. 1, band may have a second sleeve 116 at a side end portion of the band. The second sleeve is a double layer construction formed by connecting a piece of film 106 to strap 108 of the band. The connection may be done by a suitable method similar to that used for constructing the first sleeve.

The material of construction of the films or sheets used to fabricate the strap, the balloons and the sleeves of the band 100 is preferably substantially transparent whereby patient's arm can be seen through the band. Examples of the material of construction include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicones, polyurethanes various thermoplastic elastomers such as polyamide elastomers, polyurethane elastomers and polyester elastomers, and any combinations of the above in the form of, for example, resin blends, polymer alloys or laminates.

The sheet making up the band may be of any suitable thickness. In one embodiment, the thickness of the sheet material is in the range of about 0.1 to about 0.5 mm, and in some embodiments about 0.2 to about 0.3 mm. The band can be secured using hook and loop type fasteners or other suitable fasteners such as buttons, clips and buckles.

The frame 200 (see FIG. 2) is curved at both proximal and distal ends, the curvature being toward an inner peripheral side. In one embodiment, the radius of curvature $R_1$ at the proximal end is nearly the same as the radius of curvature $R_2$ at the distal end. In another embodiment, the frame is symmetrical about its center. In one embodiment, the frame is constructed of a material more rigid than the band, but maintains some flexibility whereby the frame conforms to the contour of the wrist and flexes with the expansion and contraction of balloons. In another embodiment, the frame maintains a substantially fixed shape.

In one embodiment, the frame 200 in FIG. 2 may be constructed out of material that is substantially transparent. In another embodiment, the material of construction of the frame may not be transparent. Examples of materials of construction of the frame include acrylic resins, polyvinyl chloride (rigid polyvinyl chloride and flexible polyvinyl chloride), polyolefins such as polyethylene, polypropylene and polybutadiene, polystyrene, poly(4-methyl-1-pentene), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic and aliphatic polyamides, and fluorocarbon resins such as polytetrafluoroethylene. The frame may also be made of a metal or metal alloy.

The frame 200 has gaps between the rungs 221 to provide visibility of the puncture site. The rungs are held between two beams 223 and 225. The rungs and beams can have various shapes, e.g., circular, square, rectangular and elliptical. In one embodiment, the frame is entirely curved. In another embodiment, the frame is straight in the center and curved at its ends. In one embodiment, rungs 221 are circular and each rung has a diameter of about 2 mm. In another embodiment, beams 223, 225 are also circular with diameter of about 3 mm. In yet another embodiment, the gap 204 between the rungs is about 2 mm. In one embodiment, the width of the frame is about 4 mm less than the width of the strap 108 of the band 100 in FIG. 1.

In another embodiment of the invention (See FIG. 3), hemostatic device comprises a flexible band 300. The band has a flexible strap 308 having an inner peripheral side and adapted to be wrapped and secured using binders 312 and 314 around a limb of a patient at a site on the limb where bleeding is to be stopped, a plate 304 made of a material more rigid than the band and at least a portion of the plate is curved toward its inner peripheral side at proximal and distal ends of the plate. In one embodiment, the plate 304 is of substantially fixed shape. In another embodiment, the plate 304 is flexible and does not maintain a substantially fixed shape. The material of construction of plate 304 is same as material of construction of frame 200 discussed before. In one embodiment, the plate 304 is placed in a sleeve 318 formed by a covering 310 attached to the strap 308 on the outer peripheral side of the strap at a center portion of the band. In another embodiment, both the covering 310 and the strap 308 are made of flexible plastic and are transparent. The covering 310 can be attached to strap 308 using known techniques, for example ultrasonic welding. In one embodiment, in addition to the center portion of the band, at least one side end portion of the band has a sleeve 316. The sleeve at a side end portion of the band may also be a double layer construction formed by connecting a piece of film 306 to strap 308 on the outer peripheral side of the strap 308. The connection may be done by a suitable method similar to that used for constructing the sleeve at center portion of the band. The plastic sheet material used to make the strap of the band could also be used to make the sleeves.

The first balloon 301 is provided on the inner peripheral side at a position deviated to the center portion of the curved plate from the first end of the curved plate in lengthwise direction of the band, and the first balloon is connected to the strap 308 by a connector 302 on a side of the first balloon adjacent the center portion of the curved plate. The first balloon inflates when a fluid is introduced therein. The second balloon 303 is provided on the inner peripheral side of the curved plate at a position deviated to an edge of the curved plate from the center portion of the curved plate in widthwise direction of the band, and the second balloon is connected to the strap 308 by a connector (not shown) on a side of the second balloon adjacent the edge of the curved plate. The second balloon 303 inflates when the fluid is introduced therein. In one embodiment, the band 300 is adapted to be wrapped around the wrist with a surface fastener, e.g., Hook and Loop 312 and 314 for securing the band around the wrist.

The plate 400 (see FIG. 4) is curved at both proximal and distal ends, the curvature being toward an inner peripheral side. In one embodiment, the radius of curvature $R_1$ at the proximal end is nearly the same as the radius of curvature $R_2$ at the distal end. In another embodiment, the plate 404 is symmetrical about its center. In one embodiment, the plate is constructed of a material more rigid than the band, but maintains some flexibility whereby the plate conforms to the contour of the wrist and flexes with the expansion and contraction of balloons. In another embodiment, the plate maintains a substantially fixed shape. The plate 400 may be constructed using same materials as used to construct frame 200 in FIG. 2. In one embodiment, the thickness of plate is about 2 mm. The width of the plate may be about 4 mm less than the width of the strap of the band, thereby keeping on either side of the plate a gap of about 2 mm between the edge of the plate and the edge of the strap of the band.

In another embodiment of the invention (See FIG. 5), hemostatic device 500 comprises a flexible band. The band has a flexible strap 508 having an inner peripheral side and adapted to be wrapped and secured using binders 512 and 514 around a limb of a patient at a site on the limb where bleeding is to be stopped. The band has a center portion and two side portions on either side of the center portion. In one embodiment, the center portion has a first sleeve 518 formed by a covering 510 attached to strap 508. A compression member (not shown) is placed in the first sleeve 518. In one embodiment, the compression member is a curved frame (see FIG. 2). In another embodiment, the compression member is a curved plate (see FIG. 4). In one embodiment, both the covering 510 and the strap 508 are made of flexible plastic and are transparent. The covering 510 can be attached to strap 508 using known techniques, for example ultrasonic welding. A first balloon 501 is provided on the inner peripheral side at a position deviated to the center portion of the first sleeve 518 from the proximal end of the first sleeve in lengthwise direction of the band, and the first balloon is connected to the strap 508 of the band by a connector 502 on a side of the first balloon adjacent the center portion of the first sleeve 518. In one embodiment, the width of the first balloon is nearly the same as the width of the strap 508 of the band, and the length of the first balloon is about half the length of the first sleeve 518. The first balloon 501 inflates when a fluid is introduced therein. The second balloon 503 is provided on the inner peripheral side of the first sleeve 518 at a position deviated to an edge of the first sleeve from the center portion of the first sleeve in widthwise direction of the band, and the second balloon is connected to the strap 508 of the band by a connector 504 on a side of the second balloon adjacent an edge of the first sleeve 518. The width of the second balloon is about half the width of the strap 508 of the band and the length of the second balloon is about half the length of the first sleeve 518. In another embodiment, the width of the second balloon is about 70% of the width of the band. In yet another embodiment, the width of the second balloon is about 60% of the width of the band. In a further embodiment, the width of the second balloon is about 50% of the width of the band. The second balloon 503 inflates when the fluid is introduced therein.

The material of construction of the balloons is preferably transparent and may be the same as used to make the band. In one embodiment, the material of construction of the balloon could be sheets of thickness similar to that used to make the strap of the band. In another embodiment, the sheets used to make balloons could be thinner than the sheets used to make the strap of the band. In one embodiment, the strap is made of polyvinyl chloride film of thickness 20 mils (0.508 mm) and a balloon is made of polyvinyl chloride film of thickness 10 mils (0.254 mm). The balloons could have any shape such as square, rectangular, circular and elliptical. The balloons can be made by sealing sheet cut to appropriate shape and sealed at the edge using sealing technique such as adhesion or welding. The balloons are connected to the band by flexible connectors 502 and 504 that could be made of same material as the balloon and the band. In one embodiment, the band and the compression member are substantially transparent. In another embodiment, the balloon 503 is made of translucent or opaque material and the balloon 501 is made of substantially transparent material.

As shown in FIG. 5, the first balloon 501 has connected thereto a tube 521 for introducing a fluid into the first balloon, and the second balloon 503 has connected thereto a tube 525 for introducing a fluid into the second balloon. In one embodiment, the tubes are transparent and flexible. Tube 521 is connected at a proximal end thereof to the first balloon 501 at 522. Tube 525 is connected at a proximal end thereof to the second balloon 503 at 526. Tube 521 may include an adapter 523 that is connected to the distal side of the tube, and tube 525 may include an adapter 527 that is connected to the distal side of the tube. In one embodiment, adapter 523 is identifiably different from adapter 527 so that a user knows to select the appropriate adapter that connects to the balloon user wants to inflate. The identifiable differentiation of the adapters may be through visual distinction comprising color, shape, texture or combination thereof. Inflation of the balloon is carried out by inserting the protruding tip of a syringe (not shown) into the adapter and pushing a plunger on the syringe so as to introduce fluid within the syringe through the inflator into the balloon. Once fluid has been injected into the balloon and the protruding tip of the syringe is withdrawn from the adapter, a check valve within the adapter closes, preventing the fluid from leaking out and thus maintaining the balloon in an inflated state. In another embodiment, a two-way or three-way valve is used to direct the flow of fluid into and out of the balloon, and to prevent the fluid from leaking out and thus maintaining the balloon in an inflated state.

In one embodiment, in addition to the center portion of the band, at least one side end portion of the band has a sleeve. As shown in FIG. 5, the band may have a second sleeve 516 at one side end portion of the band. The second sleeve is a double layer construction formed by connecting a piece of film 506 to strap 508 of the band. The connection may be done by a suitable method similar to that used for constructing the first sleeve. The second sleeve 516 may be used to hold tubes 521, 525 and adapters 523, 527 when the band is wrapped around the wrist of a patient (See FIG. 8).

The technique of providing a compression member on the band is not limited to the illustrated arrangement, and may involve joining the compression member(s) to the inside surface or outside surface of the band by a suitable method such as welding or adhesion. It is not necessary that the band encircle the limb, e.g., wrist completely. For example, another arrangement may be the band is held in place by tie down that holds the band firmly on the wrist. In another embodiment, the band does not have any compression member to enhance rigidity.

FIG. 6 is a sectional view showing a band in a wrapped state to the wrist 611. The band is attached to the wrist by connecting together surface fasteners (e.g. hook and loop fasteners) 612 and 614. Other means for securing the band in a wrapped state around the wrist include buttons, clips, snaps, zippers, and buckles through which the ends of the band pass. A frame 604 is placed in a sleeve formed by a covering 610 attached to the strap 608 on the outer peripheral side of the strap at a center portion of the band. One side of balloon 601 is connected to the strap 608 of the band by connector 602 at a position deviated to the center portion of the curved frame 604 from the end of the curved frame in lengthwise direction of the band. As a result, the balloon assumes an orientation whereby the pressing force F1 applied to the puncture site on the radial artery 605 acts generally in an outward direction away from the center portion of the wrist (See FIG. 6A). Consequently, force F1 does not have an impact at the location of the ulnar artery 607. On the other hand, if the balloon 601 was connected to the band at a position deviated to the end of the curved frame, the balloon would assume an orientation whereby the pressing force would be in an oblique direction towards the center portion of the wrist whereby a component of the force F1 would affect the ulnar artery 607.

The ulnar artery 607 is compressed by balloon 603, which is provided on the inner peripheral side of the curved frame 604 at a position deviated to an edge of the curved frame from the center portion of the curved frame in widthwise direction of the band, and balloon 603 is connected to the band by a connector 606 on a side of balloon 603 adjacent to an edge of the curved frame 604 (see FIG. 6B). In the present embodiment where one side of balloon 603 is connected by a connector at an edge of the band and the width of the balloon 603 is shorter than the width of the strap 608, balloon 603 assumes an orientation whereby component of the force F2 in the cross-sectional plane of the wrist is generally vertical (see FIG. 6A). The force F2 may have a component in a direction towards the elbow, but a negligible component in a direction towards the radial artery. Therefore, operation of balloon 603 to pressurize or depressurize the ulnar artery will not generally affect operation of balloon 601 to pressurize or depressurize the radial artery, and vice versa.

FIG. 7 is a schematic of a band 708 wrapped around a wrist whereby balloon 701 compresses the radial artery 705 and balloon 703 compresses the ulnar artery 707. In the embodiment in FIG. 7, the balloon 703 is located at or near the base of the palm (Guyon's canal) 704 thereby compressing the ulnar artery 707 at a location where it is most accessible for compression and the balloon 701 is located over the puncture site, which is generally about 2 cm. from the base of a palm. The pressure applied to the radial artery and the ulnar artery could be simultaneously and independently manipulated to optimize the pressure at which the bleeding from the radial artery stops while at the same time a high enough pressure is applied to the ulnar artery to prevent or minimize occlusion of the radial artery. In one embodiment, mark or marks (not shown) may be placed on the radial balloon 701 to help a user visually place a central portion of the radial balloon 701 on the radial artery 705 at or near the puncture site of the artery. Mark or marks may also be placed on the compression member and the sleeve holding the compression member to help a user in the placement of the radial balloon 701 on the puncture site. Mark may be a dot, a line, a square, a triangle or any other shape that helps in the placement.

FIG. 8 is a schematic illustration showing an anterior view (FIG. 8A) and a posterior view (FIG. 8B) of an embodiment of a band 808 wrapped around the wrist of a patient. One side of radial balloon 801 is connected to the band by connector 832 such that the connector 832 is positioned towards the center portion of the wrist. The radial balloon 801 is inflated or deflated by passing fluid (a gas such as air or a liquid such as saline) through tube 821 using a syringe (not shown) that is connected to adapter 823. The ulnar balloon 803 is inflated or deflated by passing fluid (a gas such as air or a liquid such as saline) through tube 825 using a syringe (not shown) that is connected to adapter 827. A balloon will inflate when a fluid is introduced therein, thereby applying pressure to the skin of the patient where the balloon is located. In one embodiment, the fluid is introduced using a syringe. The syringe may have markers to determine the amount of fluid that will be inserted into a balloon. The syringe may also have an outlet that can be connected to a pressure measuring device such as a manometer. In another embodiment, the balloons may have an outlet that can be connected to a pressure measuring device. The pressure measurement helps the user to inflate the balloon to a pressure that is not significantly higher than the systolic pressure of the patient, thereby allowing robust hemostasis but preventing grossly excessive compression by inordinate pressure, thereby lowering the probability of lumen compression to the point of occlusion, and flow cessation.

The edge of the band is positioned close to the base of the palm 834. The band 808 may have a sleeve 806 at a side end portion of the band. The sleeve is a double layer construction and tubes 821, 825 and adapters 823 and 827 may be inserted in the sleeve 806 so that the tubes do not dangle when a patient moves his/her hand.

Figure 9:
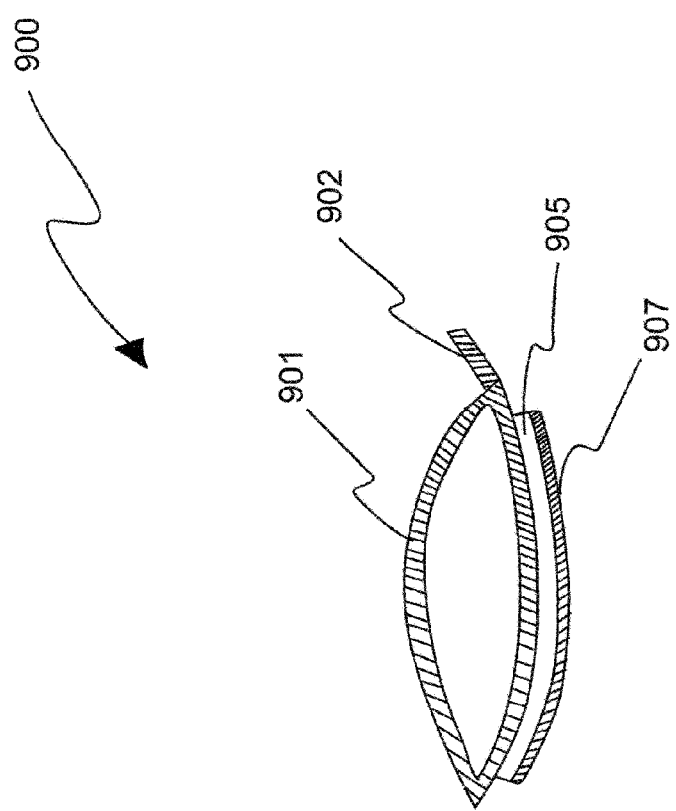
FIG. 9 is a schematic view of a balloon 900 wherein a surface of the balloon to be in contact with skin is disposed with a composition 905 and a liner 907.

FIG. 9 shows an embodiment of balloon 900 where the surface of the balloon 901 in contact with skin is coated with a composition 905. In one embodiment, composition 905 may comprise a hydrocolloid adhesive or zinc oxide-based adhesive that can be advantageously used upon the surface of the balloon when pressing the balloon on the skin of the patient. The hydrocolloid or zinc oxide-based adhesive can be used either alone or in combination with another medical grade adhesive. Hydrocolloid and zinc oxide-based adhesives have less of a tendency to excoriate the skin of a patient when removed. This can be particularly important for patients whose skin is more sensitive or fragile. In one embodiment, the coated composition 905 has a peel-off laminate (liner) 907 that is removed before placing the balloon on the puncture site. In another embodiment, the composition also contains antimicrobials. In one embodiment, the composition contains oil. Such compositions are known in the art and commercially available. See, e.g., compositions and laminates sold by Vancive Medical Technologies, Avery Dennison business. In some embodiments, connector 902 may be provided to connect the balloon to the band. In another embodiment, vasodilator medication is present on the surface of a balloon pressing on the puncture site to reduce spasm. Spasm is thought to play a role in the process of interruption of the flow that then leads to thrombosis and resultant lumen obliteration with fibrosis. Prevention and relief of spasm may help lower the probability of occlusion. An example of such vasodilator medication is nitroglycerine. In one embodiment, the surface of balloon in contact with the puncture site is disposed with nitroglycerine.

An embodiment of the band of the present invention is used in a method directed at minimizing occurrences of radial artery occlusion during the catheterization procedure of the radial artery. Once the catheterization procedure is complete, an ulnar pressure is applied to the ipsilateral ulnar artery at an ulnar pressure site while a sheath, e.g., a catheter, remains inserted in the radial artery. The sheath is then removed from the radial artery while maintaining the pressure to the ulnar artery. Once the sheath is removed, and while continuing to apply the ulnar pressure, pressure is applied to the radial artery at the access site to obtain hemostasis at the access site.

The radial artery and the ulnar artery are the two conduits for the flow of oxygenated blood to the hand. The arteries are interconnected and therefore form an interdependent flow network. When flow is reduced in one of the arteries, by compression for example, flow increases in the other artery. When the ulnar artery is compressed, flow in the ulnar artery is reduced, which causes an increase in pressure and flow in the radial artery.

In an embodiment, a further step includes confirming that the application of ulnar pressure has reduced blood flow through the ulnar artery. This is done by monitoring flow of the ulnar artery prior to and after applying the ulnar pressure.

In a further embodiment, monitoring flow of the ulnar artery includes sensing skin blood flow and/or pulsation at a fingertip or other location downstream of the ulnar pressure site. Digital plethysmography is employed in one embodiment.

In another embodiment, the method further includes confirming patency of the radial artery during the step of applying a pressure to the radial artery. Confirmation of patency is accomplished by sensing skin blood flow and/or pulsation at a fingertip or other location downstream of the access site. Other sensing locations both upstream and downstream may be used to confirm patency of the radial artery. In one embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Metric is understood to mean a sensible, quantifiable value or reading, relating to the characteristic sensed. Preferably, the previously sensed metric is read after applying the ulnar pressure step and before the step of removing the sheath from the radial artery. Digital plethysmography may be employed to obtain the metrics. Other sensing modes may be employed, so long as the selected mode is capable of confirming patency in one form or another.

Example 1

A band was fabricated from a substantially transparent polyvinyl chloride sheet material having a thickness of 0.5 mm. The band had a length of 240 mm and a width of 55 mm. A radial artery balloon and an ulnar artery balloon were each fabricated from a substantially transparent polyvinyl chloride sheet material having a thickness of 0.25 mm. The radial artery balloon had the dimension of 38 mm×55 mm and the ulnar artery balloon had the dimension of 38 mm×38 mm. The radial artery balloon, ulnar artery balloon and band were welded together at the necessary places to form a hemostatic device having the construction according to FIG. 5. Two adapters with check valves were connected to the two balloons via ducts as shown in FIG. 5. The adapters were configured to lock with a luer lock syringe. A curved frame was made of 2 mm diameter rungs, with spacing between the rungs of 2 mm (center to center distance between the rungs was 4 mm). The rungs were held between two parallel beams of diameter 3 mm. The frame was curved at both ends, and had identical radius of curvature at both ends. The radius of curvature at each end was 20 mm. The frame had a center portion that was straight and had a length of 28 mm. The width of the frame was 52 mm. The frame was constructed according to FIG. 2. Hook and loop (Velcro) fasteners were used to fasten. This hemostatic device was wrapped around the wrist of normal volunteers and the two balloons were inflated by injecting air into the balloons using a 20 mL syringe with a luer lock. It was observed that inflation of the radial balloon did not influence perfusion of the fingers via the ulnar artery. A 20 mL inflation of the radial artery balloon lead to complete obliteration of antegrade radial flow, although there was no influence on perfusion through the ulnar artery. On the ulnar side, with a shorter width (38 mm) balloon, full 15 mL inflation of ulnar balloon did not influence the status of flow in the radial artery.

Any constricting girdle-like device would be expected, even at a lower pressure to first constrict the veins and cause venous congestion in the fingers. It was surprising to observe a complete lack of venous congestion, and no symptoms of venous congestion were reported by any of the volunteers. On several occasions, 2 hour application of the band was performed as would be performed clinically for hemostasis. Venous congestion did not occur. Symptoms related to pressure at the ulnar tuberosity were also not reported by the volunteers. This is likely because of (i) focal pressure application by the orientation of the balloons, leaving probably enough soft tissue space (in the central compartment of the forearm where most large veins are located) for the venous return to occur, and (ii) a decrease in magnitude of required pressure because of the design features such as orientation and sizes of the two balloons, their location in the band, and the shape and structure of the frame.

Comparative Example 2

A band similar to that used in EXAMPLE 1 was fabricated, the only difference being, in COMPARATIVE EXAMPLE 2, the width of the ulnar balloon was nearly the same as the width of the band. In EXAMPLE 1, the ulnar balloon had a width of 38 mm, which is about 70% of the width of the band. With the larger ulnar balloon of COMPARATIVE EXAMPLE 2, inflation of the ulnar balloon was noted to influence the perfusion of radial artery. This was particularly pronounced in small forearms where the larger ulnar balloon may assume an orientation such that the force applied to the wrist when the ulnar balloon is inflated impacts the radial artery.

Tests have shown that the location of the ulnar balloon on the forearm aspect of the band increased the efficacy of the balloon to compress and occlude ulnar artery. Moving the balloon towards the hand and especially gluing it to the palmar aspect of the band increased the efficacy of the ulnar balloon to focally compress and occlude ulnar artery without any other effects or symptoms.

It will be appreciated that several of the above-disclosed and other features and functions, or alternatives or varieties thereof, may be desirably combined into many other different systems or applications. Also that various alternatives, modifications, variations or improvements therein may be subsequently made by those skilled in the art which are also intended to be encompassed by the following claims.

In the description above, for the purposes of explanation, numerous specific requirements and several specific details have been set forth in order to provide a thorough understanding of the embodiments. It will be apparent however, to one skilled in the art, that one or more other embodiments may be practiced without some of these specific details. The particular embodiments described are not provided to limit the invention, but to illustrate it. The scope of the invention is not to be determined by the specific examples provided above. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. In another situation, an inventive aspect may include a combination of embodiments described herein or in a combination of less than all aspects described in a combination of embodiments.

The invention claimed is:

1. A hemostatic device comprising:
    a band adapted to be wrapped around a wrist of a patient at a puncture site on the wrist where bleeding is to be stopped;
    a fastener for securing the band in a wrapped state to the patient's wrist;
    a compression member having an inner peripheral side, the compression member is made of a material such that the compression member is more rigid than the band, and at least a portion of which is curved toward the inner peripheral side;
    the compression member possessing a first curved portion in a first half of the compression member located between a center and a first end of the compression member, a second curved portion in a second half of the compression member located between the center and a second end of the compression member, and an axis traversing from the first end of the compression member, through the center, to the second end of the compression member;
    a first balloon provided on the inner peripheral side in the first half of the compression member at a position offset to the center of the compression member from the first end of the compression member, the first balloon comprising a plurality of linear sides and is connected to the band by a first connector only on a first linear side of the first balloon; and
    a second balloon provided on the inner peripheral side in the second half of the compression member, the second balloon comprising a plurality of linear sides and is connected to the band by a second connector only on a first linear side of the second balloon.

2. The hemostatic device of claim 1, wherein the first linear side of the first balloon is adjacent the center of the compression member.

3. The hemostatic device of claim 2, wherein the first linear side of the first balloon is perpendicular to the axis of the compression member.

4. The hemostatic device of claim 1, wherein the second balloon is at a position offset to an edge of the compression member from the center of the compression member.

5. The hemostatic device of claim 4, wherein the first linear side of the second balloon is adjacent the edge of the compression member.

6. The hemostatic device of claim 5, wherein the first linear side of the second balloon is parallel to the axis of the compression member.

7. The hemostatic device of claim 1, wherein the compression member is a curved frame comprising a plurality of rungs.

8. The hemostatic device of claim 1, wherein the compression member is a curved plate.

9. The hemostatic device of claim 1, wherein the width of the first balloon is about the same as the width of the band and the width of the second balloon is less than the width of the band.

10. The hemostatic device of claim 9, wherein the width of the second balloon is less than 70% of the width of the band.

11. The hemostatic device of claim 1, wherein the band, the compression member, and the first balloon are made of substantially transparent material, such that the site where bleeding is to be stopped may be viewed through the band, through the compression member, and through the first balloon.

12. The hemostatic device of claim 1, wherein a radius of curvature of the first curved portion of the compression member is nearly the same as a radius of curvature of the second curved portion of the compression member.

13. The hemostatic device of claim 1, further comprising a first sleeve including a double layer construction defining a compression member holder, and the compression member is positioned in a gap in the double layer construction such that the compression member is held in the compression member holder of the band.

14. The hemostatic device of claim 13, further comprising a first tube communicating with an interior of the first balloon, a first adapter connected to the first tube and into which a first syringe is insertable to introduce a first fluid in the first syringe into the first balloon by way of the first tube, and a second tube communicating with an interior of the second balloon, a second adapter connected to the second tube and into which a second syringe is insertable to introduce a second fluid in the second syringe into the second balloon by way of the second tube.

15. The hemostatic device of claim 14, further comprising a second sleeve including a double layer construction defining an adapter holder for the first adapter and the second adapter, and the first adapter and the second adapter are positioned in a gap in the double layer construction such that the first and the second adapter are held in the adapter holder of the band.

16. The hemostatic device of claim 14, wherein the first adapter is identifiably different from the second adapter, wherein the identifiable difference comprises color, shape, texture or combination thereof.

17. The hemostatic device of claim 1, further comprising a marker for positioning the first balloon at the site where bleeding is to be stopped.

18. The hemostatic device of claim 1, wherein a surface of the first balloon that will contact skin at the puncture site is disposed with at least a vasodilator medication.

19. The hemostatic device of claim 1, wherein the fastener comprises a hook material and a loop material, wherein the hook material is placed at a first end of the band and the loop material is placed at a second end of the band.

20. The hemostatic device of claim 1, wherein the width of the band is greater than 40 mm.

21. A hemostatic device comprising:
    a band adapted to be wrapped around a wrist of a patient at a puncture site on the wrist where bleeding is to be stopped;
    a fastener for securing the band in a wrapped state to the patient's wrist;
    a compression member having an inner peripheral side, the compression member is made of a material such that the compression member is more rigid than the band, and at least a portion of which is curved toward the inner peripheral side;
    the compression member possessing a first curved portion in a first half of the compression member located between a center and a first end of the compression member, a second curved portion in a second half of the compression member located between the center and a second end of the compression member, and an axis traversing from the first end of the compression member, through the center, to the second end of the compression member;

a first balloon provided on the inner peripheral side in the first half of the compression member at a position offset to the center of the compression member from the first end of the compression member, the first balloon comprising a plurality of linear sides and is connected to the band by a first connector only on a first linear side of the first balloon, said first linear side of the first balloon being adjacent the center of the compression member; and a second balloon provided on the inner peripheral side in the second half of the compression member at a position offset to an edge of the compression member from the center of the compression member, the second balloon comprising a plurality of linear sides and is connected to the band by a second connector only on a first linear side of the second balloon, said first linear side of the second balloon being adjacent the edge of the compression member.

22. The hemostatic device of claim 21, wherein the first linear side of the first balloon is perpendicular to the axis of the compression member.

23. The hemostatic device of claim 21, wherein the first linear side of the second balloon is parallel to the axis of the compression member.

24. The hemostatic device of claim 21, wherein the compression member is a curved frame comprising a plurality of rungs.

25. The hemostatic device of claim 21, wherein the compression member is a curved plate.

26. The hemostatic device of claim 21, wherein the width of the first balloon is about the same as the width of the band and the width of the second balloon is less than the width of the band.

27. The hemostatic device of claim 21, wherein a radius of curvature of the first curved portion of the compression member is nearly the same as a radius of curvature of the second curved portion of the compression member.

28. A hemostatic device comprising: a band adapted to be wrapped around a wrist of a patient at a puncture site on the wrist where bleeding is to be stopped;

a fastener for securing the band in a wrapped state to the patient's wrist;

a curved frame having an inner peripheral side, the curved frame comprising a plurality of rungs and is made of a material such that the curved frame is more rigid than the band, and at least a portion of which is curved toward the inner peripheral side;

the curved frame possessing a first curved portion in a first half of the curved frame located between a center and a first end of the curved frame, a second curved portion in a second half of the curved frame located between the center and a second end of the curved frame, and an axis traversing from the first end of the curved frame, through the center, to the second end of the curved frame;

a first balloon provided on the inner peripheral side in the first half of the curved frame at a position offset to the center of the curved frame from the first end of the curved frame, the first balloon comprising a plurality of linear sides and is connected to the band by a first connector only on a first linear side of the first balloon, said first linear side of the first balloon being adjacent the center of the curved frame and perpendicular to the axis of the curved frame; and a second balloon provided on the inner peripheral side in the second half of the curved frame at a position offset to an edge of the curved frame from the center of the curved frame, the second balloon comprising a plurality of linear sides and is connected to the band by a second connector only on a second linear side of the second balloon adjacent the edge of the curved frame and parallel to the axis of the curved frame.

29. The hemostatic device of claim 28, wherein the width of the first balloon is about the same as the width of the band and the width of the second balloon is less than the width of the band.

30. The hemostatic device of claim 28, wherein a radius of curvature of the first curved portion of the curved frame is nearly the same as a radius of curvature of the second curved portion of the curved frame.

* * * * *